US00PP23700P3

(12) United States Plant Patent
Schoone

(10) Patent No.: US PP23,700 P3
(45) Date of Patent: Jul. 2, 2013

(54) ***PHALAENOPSIS* ORCHID PLANT NAMED 'CONFIDENCE'**

(50) Latin Name: ***Phalaenopsis* hybrid**
Varietal Denomination: Confidence

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 13/137,368

(22) Filed: Aug. 9, 2011

(65) Prior Publication Data

US 2012/0102610 P1 Apr. 26, 2012

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named 'Confidence' characterized by flowers which are white with a purple blush in the center and some yellow in the labellum; plants which may be propagated economically and uniformly using tissue culture; plants which produce more than one inflorescence; long and sturdy inflorescences; and dark-green foliage.

3 Drawing Sheets

Latin name of the genus and species of the plant claimed: *Phalaenopsis* hybrid.

Variety denomination: 'Confidence'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Confidence'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Confidence' is a product of a controlled breeding program conducted by the inventor, Rene Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Confidence' originated from a cross made by the inventor in 1998 in Strengweg, Heemskerk, The Netherlands. The female or seed parent is the *Phalaenopsis* cultivar designated 'Tom Coffey', unpatented. The male or pollen parent is the *Phalaenopsis* cultivar designated 'Pink Twilight', unpatented. The new *Phalaenopsis* 'Confidence' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Confidence', which in combination distinguish this *Phalaenopsis* as a new and distinct cultivar:

1. flowers which are white with a purple blush in the center and some yellow in the labellum.
2. plant produces more than one inflorescence;
3. plants may be propagated economically and uniformly using tissue culture;
4. inflorescences are long and sturdy; and
5. dark-green foliage.

In comparison with the parental cultivars of 'Confidence', the female parent 'Tom Coffey', has white flowers and the male parent 'Pink Twilight' has violet colored flowers, whereas the flowers of the claimed variety 'Confidence' are white with a purple haze in the center which flows out to the edges.

Presently, there is no other commercial cultivar to which 'Confidence' can be meaningfully compared.

BRIEF DESCRIPTION OF THE PHOTOGRAPHS

The accompanying photographs illustrate the overall appearance of the new *Phalaenopsis* 'Confidence' showing the colors as true as is reasonably possible with colored reproductions of this type. Colors in the photographs may differ slightly from the color values cited in the detailed botanical description, which accurately describe the color of 'Confidence'.

DETAILED BOTANICAL DESCRIPTION

Figure 1:
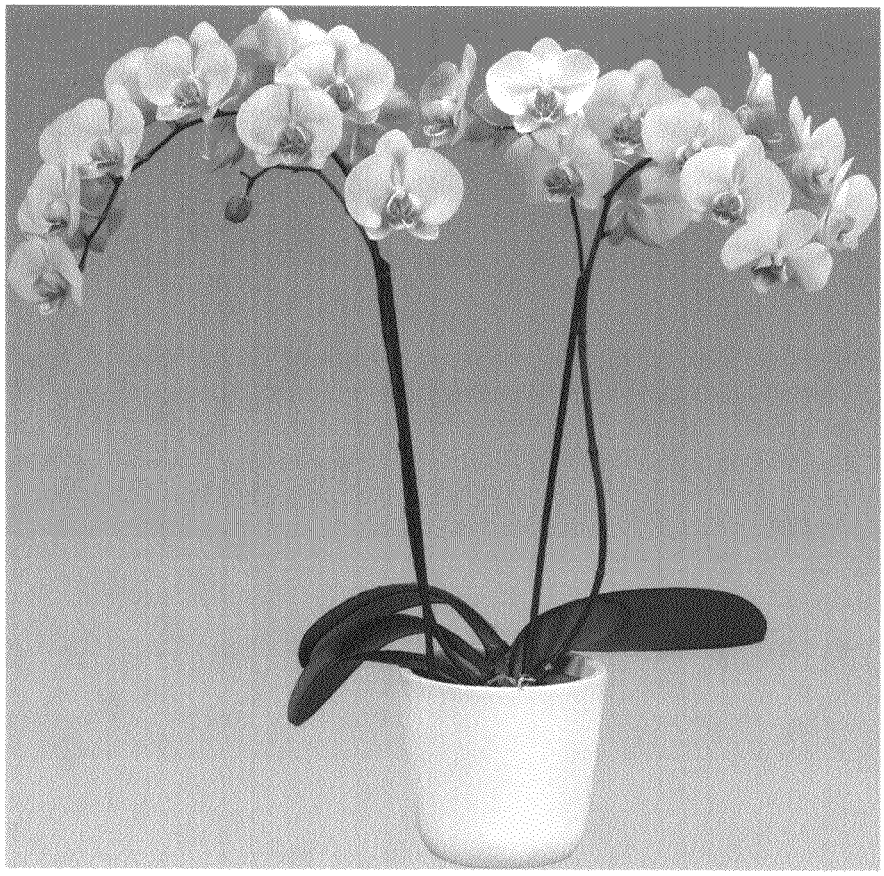
FIG. 1 shows a side view perspective of a typical flowering plant of 'Confidence' in a 12 cm pot, at 16 months of age.

The new *Phalaenopsis* cultivar 'Confidence' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Confidence' as grown in a greenhouse in Strengweg, Heemskerk, The Netherlands, under conditions which closely approximate those generally used in commercial practice. Initially, the ideal temperature to grow plants of 'Confidence' is 27° C. during the day and at night. Then, during the flowering phase of 'Confidence', the ideal growing temperature is 20-22° C. during the day and 18° C. at night. Light levels for growing 'Confidence' are a minimum of 5,000 lux and a maximum of 10,000 lux. A balanced fertilizer with level of 200 ppm N, 87 ppm P, 168 ppm K is applied. Duration of growth of 'Confidence' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Confidence' plants described is 12 months after potting.

Classification:

*Botanical.*—*Phalaenopsis* hybrid.

Parentage:

*Female or seed parent.*—*Phalaenopsis* cultivar designated 'Tom Coffey', unpatented.

*Male or pollen parent.*—*Phalaenopsis* cultivar designated 'Pink Twilight', unpatented.

Propagation:

*Type.*—Tissue culture.

*Rooting habit and description.*—Fleshy; approximately 5 mm-8 mm wide and green in color; freely branching. It takes 12 weeks for plants growing in tissue culture to initiate roots.

Plant:

*Size at maturity.*—Height: about 68 cm. Spread: about 55 cm.

*Growth habit.*—Standard; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 5 to 8 leaves are produced before flowering.

*Arrangement and attachment.*—Half up/horizontal and on two sides.

*Overall shape of leaf.*—Oval, the tip is blunt and asymmetric.

*Texture* (*upper & underside*).—Smooth and leathery.

*Pubescence.*—3 to 4 pairs of leaves.

*Mature leaf length.*—About 24 to 29 cm.

*Mature leaf width.*—About 9 cm.

*Mature leaf thickness.*—About 2 mm.

*Mature leaf color.*—Upper side: RHS 146A, at the leaf base and on the edges red/purple RHS 59A; under side: green RHS 146A; the midvein, and the edges are RHS 187A with a haze of RHS 187A.

*Leaf base.*—Acute.

*Margin.*—Entire.

*Venation.*—Pattern: parallel. Color of midvein: upper side: dark green RHS N137A; under side RHS 187A.

Raceme:

*Quantity per plant.*—About 1 to 2.

*Number of flowers per raceme.*—About 22 to 28.

*Length.*—About 60 to 70 cm.

*Diameter.*—About 7 mm.

*Strength.*—Strong.

*Aspect.*—Upright.

*Texture.*—Glabrous and smooth.

*Color.*—Green RHS 148A.

*Internode.*—Length: about 40 mm to 48 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 mm to 22 mm. Diameter (at midpoint): about 13 mm to 20 mm. Shape: egg-shaped. Color: combination between green RHS N144D and purple RHS N74D.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
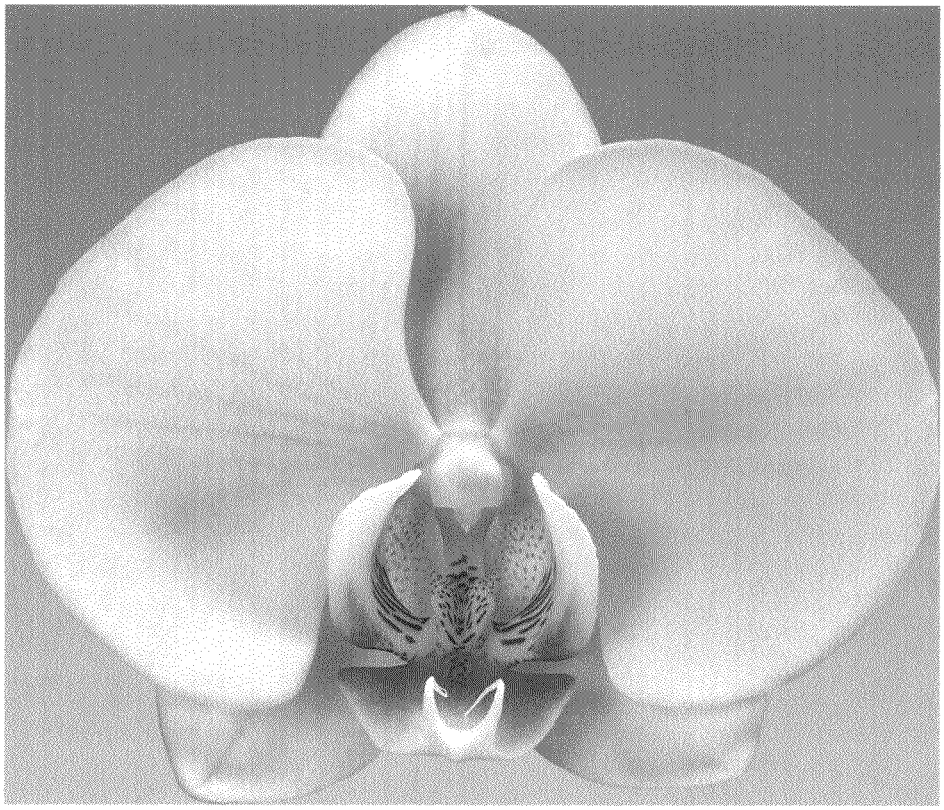
FIG. 2 shows a close-up view of the typical buds and flowers of 'Confidence'.
Figure 3:
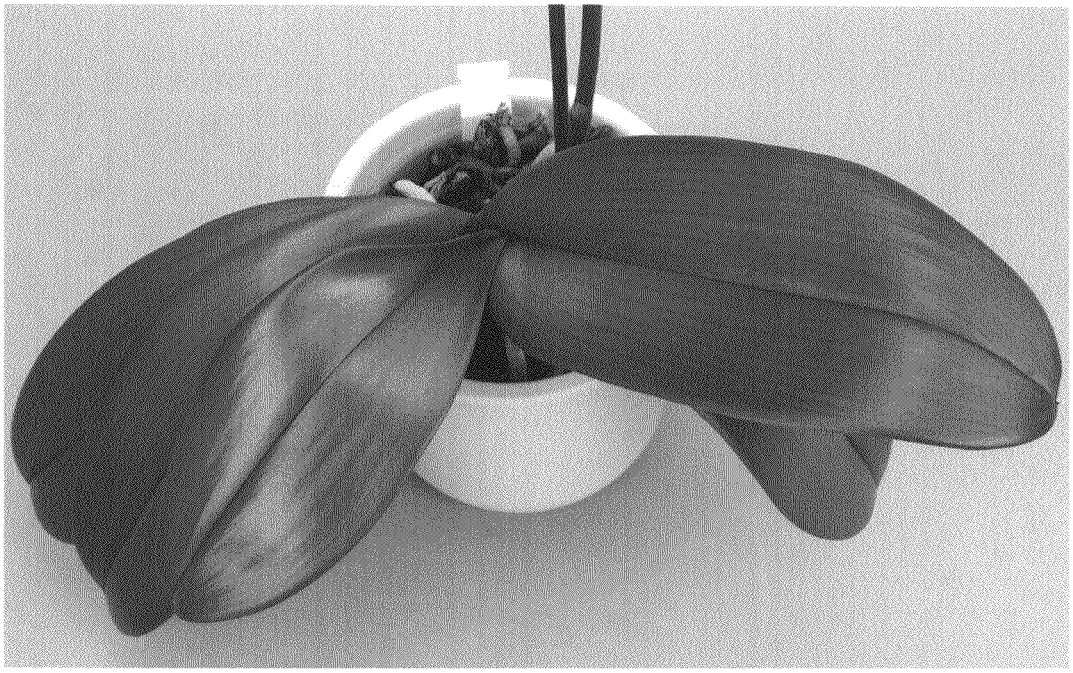
FIG. 3 shows a close-up view of the typical leaves of 'Confidence'.

*Flower.*—Rate of opening: Flowers fully opened about 2 to 3 days after petal and sepal separation. Orientation at opening: slanted upward and outward. Shape: see FIG. 2. Size: Height: about 50 mm. Diameter: about 70 mm. Depth of tube: about 18 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: oval. Margin: entire and weakly undulate. Base: broadly ovate. Length: about 40 mm. Width: about 30 to 35 mm. Texture: Upper surface: smooth and satiny. Under surface: smooth and satiny. Color (when fully opened): upper side: White RHS NN155C, with a purple blush in the center RHS N74D which flows out. under side: White RHS NN155C with a purple blush RHS 76C. Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: lateral lobes: oval. midlobe: round corners. Length: about 25 mm. Width (not flattened): about 21 mm. Texture: Upper & under surface: smooth and satiny. Color (when fully opened): Upper surface: The main color is white RHS NN155C. At the base of the lateral lobes purple/red stripes and spots RHS 72A and at the bottom edges yellow RHS 12B with some purple/red RHS 64A. The base of the mid lobe is yellow RHS 13B with purple/red spots RHS 72A and some RHS 76A which flows out on to the white. The corners are also yellow RHS 13B with some red/purple RHS 64A. Chirri are white (as main color). Under surface: Lateral lobes are white RHS NN155C with a purple haze RHS 75C. At the bottom some yellow RHS 8B and red/purple RHS 64A. Midlobe is white RHS NN155C with at the base some purple RHS N80A which flows out into RHS N80B. On the sides some yellow RHS 14B and some red/purple RHS 64A. Chirri: are medium size (about 11 mm). Pestle (Callosities): Length: about 4 mm. Width (not flattened): about 5 mm. Height: about 7 mm. Color: yellow RHS 13B with purple/red spots RHS72A.

*Sepals*.—Arrangement: Outer whorl comprises 3 sepals. Overall shape: elliptical and weakly cupped. Margin: entire and weakly undulate. Length: about 33 mm. Width: about 22 mm. Apex: oval. Texture: Upper & under surface: smooth and satiny. Color (when fully opened): upper surface: White RHS NN155C with a purple haze RHS 76A. At the base of the lateral sepals are purple spots RHS N80B. under surface: white RHS NN155C with a purple haze RHS 75A.

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 5 mm. Color: purple RHS 76C.

*Pollinia*.—Quantity: Two. Diameter: about 1 mm. Color: orange/yellow RHS 23A.

*Ovary*.—Length: about 5 mm. Diameter: about 5 mm. Color: purple RHS 76C.

*Pedicel*.—Length: about 40 mm to 45 mm. Diameter: about 3 mm. Texture: glabrous and smooth. Color: Close to the flower purple RHS 75C and white RHS N155C; close to the raceme some brown/purple RHS 176 A; in between some green RHS 145C.

Disease/pest resistance susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'CONFIDENCE', as illustrated and described herein.

* * * * *

UNITED STATES PATENT AND TRADEMARK OFFICE

CERTIFICATE OF CORRECTION

PATENT NO. : PP23,700 P3
APPLICATION NO. : 13/137368
DATED : July 2, 2013
INVENTOR(S) : René Schoone It is certified that error appears in the above-identified patent and that said Letters Patent is hereby corrected as shown below:

ON THE TITLE PAGE, Item (30) should read:

(30) Foreign Application Priority Data

Oct. 20, 2010 (NL) .....OPS726

Signed and Sealed this
Twenty-fourth Day of September, 2013

Teresa Stanek Rea
*Deputy Director of the United States Patent and Trademark Office*